United States Patent [19]
Braye et al.
[11] 4,311,845
[45] Jan. 19, 1982

[54] PROCESS FOR THE PREPARATION OF THIENO[3,2-c]PYRIDINE

[75] Inventors: Emile H. Braye, Auterive; Jean-Marie Ollivier, Arudy, both of France

[73] Assignee: Sanofi, Paris, France

[21] Appl. No.: 219,247

[22] Filed: Dec. 22, 1980

[30] Foreign Application Priority Data

Dec. 20, 1979 [FR] France ............................ 79 31247

[51] Int. Cl.[3] ............................ C07D 495/04
[52] U.S. Cl. ............................ 546/114
[58] Field of Search ............................ 546/114

[56] References Cited

PUBLICATIONS

Hertz et al., JACS, vol. 75 (1953), p. 5122.

*Primary Examiner*—Richard Raymond
*Attorney, Agent, or Firm*—Weiser, Stapler & Spivak

[57] ABSTRACT

The present invention relates to a process for the preparation of thieno[3,2-c]pyridine, wherein 4,5,6,7-tetrahydrothieno[3,2-c]pyridine is catalytically dehydrogenated in the gaseous phase at a temperature of from about 350° to about 600° C. using a catalyst comprising at least one metal or metal oxide of which the metal component is selected from chromium, nickel, molybdenum, cobalt and tungsten, optionally in association with magnesium, sodium or iron or the oxides thereof, the catalyst being deposited on an inert carrier.

17 Claims, No Drawings

PROCESS FOR THE PREPARATION OF THIENO[3,2-c]PYRIDINE

The present invention relates to a process for the preparation of thieno[3,2-c]pyridine by catalytic dehydrogenation.

Many processes for the preparation of derivatives of thieno[3,2-c]pyridine and thieno[2,3-c]pyridine have been described in the literature but they are either difficult to carry out on an industrial scale, or very laborious, or cannot be used for the preparation of certain derivatives substituted in the cyclic system. Thus, the methods of synthesis described by W. Hertz and L. Tsai (J.A.C.S., 75, 5122/1953); by C. Hansch, W. Carpenter and J. Todd (J. Org. Chem., 23, 1924/1958); by L. H. Klemm, J. Shabtoy, D. R. McCoy and W .K. Kiang (J. Het. Chem., 5883/1968 and 6813/1969); by S. Gronowitz and E. Sandberg (Ark. Kemi., 32, 217/1970); by F. Eloy and A. Deryckere (Bull. Soc. Chim. Belges, 79, 301/1970); by J. P. Maffrand and F. Eloy (J. Het. Chem., 13, 1347/1976); by A. Heymes and J. P. Maffrand in U.S. Pat. No. 4,065,459, issued Dec. 27, 1977, which corresponds to French Pat. No. 75 17 009 and J. P. Maffrand French Pat. No. 77 18 991; and French Pat. No. 78 12 037; suffer from one or more of the above-mentioned disadvantages.

Furthermore, none of the above-mentioned references describe catalytic dehydrogenation of the kind with which the present invention is concerned.

It is an object of the present invention to provide a process which is easy to carry out and which gives good yields of thieno[3,2-c]pyridine; this compound being an important intermediate in the chemical and pharmaceutical industries and being especially useful for preparing thienopyridine compounds which have various useful activities including activity against platelet aggregation.

Thus, according to the present invention, there is provided a process for the preparation of thieno[3,2-c]pyridine, wherein 4,5,6,7-tetrahydrothieno[3,2-c]pyridine is catalytically dehydrogenated in the gaseous phase at a temperature effective for the purpose, and preferably at a temperature of from about 350 to about 600° C. using a catalyst comprising at least one metal or metal oxide, the metal component of which is selected from chromium, nickel, molybdenum, cobalt and tungsten, optionally in association with at least one of magnesium, sodium or iron or the oxides thereof; the active catalyst material being deposited on an inert carrier.

The reaction in the gaseous phase can be carried out in the presence of an inert diluent, the reaction temperature preferably being from about 350° to about 600° C. and especially preferably from about 450° to about 500° C.

The 4,5,6,7-tetrahydrothieno[3,2-c]pyridine used as the starting material may be prepared by known processes and especially by those described in our U.S. Pat. Nos. 4,127,580 and 4,174,448.

The catalytic reaction in the gaseous phase is carried out under a partial or total pressure of the tetrahydrothienopyridine of from about 5 to about 1000 mm/Hg and preferably of from about 50 to about 150 mm/Hg.

The liquid tetrahydrothienopyridine may be converted to the gaseous phase in any known manner, for example by evaporating the compound in the liquid phase while maintaining a controlled temperature and a pressure, preferably a reduced pressure, or by pre-heating the liquid in the presence of a current of inert gas, the supply and pressure of which is regulated in a manner such that the desired partial pressure of the tetrahydrothienopyridine is obtained. In the case of dilution with an inert gas, it is advantageous to operate at a total pressure equivalent to the prevailing atmospheric pressure.

The inert gas used can be, for example, nitrogen, helium, neon or argon.

The reaction is carried out by the continuous passage of the gaseous phase at an appropriate rate over the catalyst to give a contact time of from about 0.1 second to about 10 minutes and preferably of from about 1 to about 10 seconds.

The three parameters discussed above, namely, temperature, partial pressure and contact time, are governed by the known laws of kinetics and thermodynamics, which permit regulation of the reaction. Thus, for example, at a low temperature, the contact time is correspondingly longer.

The catalysts ideally suited for this dehydrogenation are based either upon one or more metals or upon oxides of these metals, the metals being selected from chromium, nickel, molybdenum, tungsten and cobalt, optionally in association with magnesium, sodium, or iron or the oxides thereof. The metals or their oxides are deposited upon appropriate inert carriers, for example alumina, activated charcoal, silica, kieselguhr or the like.

One preferred catalyst is based upon chromium oxide ($Cr_2O_3$), deposited on an inert carrier, such as alumina, in amounts varying from about 1 to about 33%, by weight, and preferably, about 15 to about 25%, by weight. The catalytic activity of the chromium oxide may be augmented by the addition of a small amount of magnesium oxide, and/or sodium oxide, iron oxide or mixtures thereof.

Another preferred catalyst which may be used for the dehydrogenation is based upon nickel or cobalt oxide and molybdenum oxide, the preferred carrier being alumina. The amount of nickel or cobalt oxide may be from about 1 to about 5%, by weight, and that of the molybdenum oxide from about 5 to about 20% by weight; in both cases based on the weight of the carrier.

A third preferred catalyst contains nickel and tungsten, the amounts of which may be, respectively, from about 3 to about 10% by weight and from about 5 to about 25%, by weight. The carrier is again preferably alumina but silica, kieselguhr or activated charcoal may also be used.

The following Examples are given for the purpose of illustrating the present invention:

EXAMPLE 1

The catalytic dehydrogenation reaction according to the present invention is carried out in a vertical tubular reactor placed in a furnace which enables temperatures above 600° C. to be achieved. The reactor comprises three zones. The lower zone is filled with Raschig rings. The central zone contains 40 ml. (36 g.) of a catalyst containing, by weight, 20% chromium oxide, 0.5% sodium oxide and 0.05% ferric oxide, the carrier being gamma-alumina and the catalyst having a contact surface area of 150 $m^2/g$. The upper zone of the reactor, above the layer of catalyst, contains a bed of "Pyrex" glass beads. The upper zone of the reactor serves to evaporate the tetrahydrothienopyridine and to bring the vapors to the chosen reaction temperature, which is the same as that of the catalyst. A series of thermocouples enable the temperature to be monitored along the length of the reactor. A trap is positioned below the lower zone of the furnace and maintained at a temperature low enough for the condensation of the emerging vapors. The upper zone of the reactor is connected to a tube into while is introduced a continuous and known current of nitrogen and to a dosing pump for supplying liquid tetrahydrothienopyridine.

The catalyst is previously activated by passing a current of nitrogen through the reactor for 18 hours, which the temperature of the catalyst bed is maintained at about 470° C.

The actual dehydrogenation reaction is carried out by regulating the delivery by the dosage pump of the liquid tetrahydrothienopyridine to about 13.9 g./hour and by regulating the delivery of nitrogen to about 18 liters/hour at 20° C., at atmospheric pressure. Under these conditions, the contact time is about 2.5 seconds and the spatial velocity is about 1300/1/hour.

The condensate obtained crystallises to a large extent at ambient temperature in the trap, a part of the vapor being entrained by the stream of nitrogen. The condensate obtained is redistilled to eliminate the small amount of coloured by-products usually formed.

Gas chromatographic analysis of the distillate indicates a conversion rate of 93% and a selectivity of about 91.6%. The crystals obtained by cooling, melt at a temperature of from about 46.5 to about 50° C. The IR and NMR spectra of the crystals are identical with those of an authentic sample of thieno[3,2-c]-pyridine.

EXAMPLE 2

Into a horizontal reactor equipped in a manner similar to that of Example 1 and containing 40 ml. of catalyst containing, by weight of the total catalyst composition, 6% nickel, 19% tungsten and 75% alumina, there are passed vapors of 4,5,6,7-tetrahydrothieno[3,2-c]pyridine at a rate of about 13.9 g./hour and at a pressure of about 90 mm/Hg absolute. In this case, the exit from the trap is connected with a vacuum pump through a water trap which is precision controlled by a needle valve, this water-trap being regulated in order to obtain the desired pressure in the reactor. A manometer may also be used in order to achieve the same result. Under these conditions, the rate of recovery is very good; the selectivity and the rate of conversion are analogous to those of Example 1.

What is claimed is:

1. A process for the preparation of thieno[3,2-c]pyridine from 4,5,6,7-tetrahydrothieno[3,2-c]pyridine which comprises catalytically dehydrogenating in the gaseous phase at a temperature effective to catalytically dehydrogenate said pyridine in the presence of a catalyst comprising at least one member selected from the group consisting of chromium, nickel, molybdenum, cobalt and tungsten and the oxides thereof.

2. The process of claim 1 which is carried out at a temperature in the range from about 350° to about 600° C.

3. The process of claim 2 wherein the catalyst is on an inert carrier.

4. The process of claim 1 wherein the catalyst also comprises at least one additional component selected from the group consisting of magnesium, sodium and iron and the oxides thereof.

5. The process of claim 2 wherein the catalytic dehydrogenation reaction is carried out at a temperature of from about 450° to about 500° C.

6. The process of claim 1 wherein the reaction is carried out at a partial or total pressure of 4,5,6,7-tetrahydrothieno[3,2-c]pyridine of from about 5 to about 1000 mm/Hg.

7. The process of claim 6 wherein the partial or total pressure of the 4,5,6,7-tetrahydrothieno[3,2-c]pyridine is from about 50 to about 150 mm/Hg.

8. The process of claim 1 wherein the contact time with the catalyst is from about 0.1 second to about 10 minutes.

9. The process of claim 8 wherein the contact time is from about 1 to about 10 seconds.

10. The process of claim 1 wherein the gaseous phase contains an inert diluent.

11. The process of claim 10 wherein the inert diluent is nitrogen, helium, neon or argon.

12. The process of claim 1 wherein the inert carrier is alumina, activated charcoal, silica or kieselguhr.

13. The process of claim 2 wherein the catalyst comprises chromium oxide ($Cr_2O_3$) deposited in an amount of from about 1 to about 33% by weight on an inert carrier and optionally contains a minor amount of at least one additional component selected from the group consisting of magnesium oxide, sodium oxide, and iron oxide.

14. The process of claim 13 wherein the catalyst comprises about 15 to about 25% by weight of chromium oxide.

15. The process of claim 1 wherein the catalyst comprises nickel or cobalt oxide in an amount of from about 1 to about 5% by weight and molybdenum oxide in an amount of from about 5 to about 20% by weight.

16. The process of claim 1 wherein the catalyst comprises about 3 to about 10% by weight of nickel and about 5 to about 25% by weight of tungsten.

17. The process claims 13, 14, 15 or 16 wherein the inert carrier is alumina.

* * * * *